United States Patent [19]
Muller

[11] Patent Number: 5,958,715
[45] Date of Patent: Sep. 28, 1999

[54] METHOD FOR QUANTITATIVE MEASUREMENT OF AN ENZYME LINKED IMMUNOSORBENT ASSAY

[75] Inventor: Robert Edwin Muller, Surrey, United Kingdom

[73] Assignee: BRF International, United Kingdom

[21] Appl. No.: 08/981,117

[22] PCT Filed: Jun. 24, 1996

[86] PCT No.: PCT/GB96/01518

§ 371 Date: Dec. 23, 1997

§ 102(e) Date: Dec. 23, 1997

[87] PCT Pub. No.: WO97/01762

PCT Pub. Date: Jan. 16, 1997

[30] Foreign Application Priority Data

Jun. 26, 1995 [GB] United Kingdom .................. 9512994

[51] Int. Cl.[6] ....................... G01N 33/535; G01N 33/557
[52] U.S. Cl. .................... 435/7.92; 435/7.9; 435/7.94; 435/25; 435/26; 435/27; 436/517
[58] Field of Search ................................ 435/7.92, 7.94, 435/25, 26, 27, 975, 7.9; 436/517

[56] References Cited

U.S. PATENT DOCUMENTS 4,496,658  1/1985  Kondo et al. ........................... 436/510
4,590,157  5/1986  Chandler et al. ........................... 435/7
4,722,893  2/1988  Shigeta et al. ............................. 435/7

FOREIGN PATENT DOCUMENTS

| 123 902 | 11/1984 | European Pat. Off. |
| 202 081 | 11/1986 | European Pat. Off. |
| 317 070 | 5/1989 | European Pat. Off. |
| 735 368 | 10/1996 | European Pat. Off. |
| WO 91 11530 | 8/1991 | WIPO |
| WO 95 27205 | 10/1995 | WIPO |

OTHER PUBLICATIONS

Billingham et al, 1991, Philosophical Transaction of the Royal Society of London, 340:569–91.

Primary Examiner—David Saunders
Attorney, Agent, or Firm—Klauber & Jackson

[57] ABSTRACT

Method of quantitative analysis of an enzyme linked immuno assay comprising the steps of forming an antigen—antibody complex between an antigen present in a sample to be tested and an enzyme labelled antibody and thereafter adding a substrate composition which can be converted into a differently colored product composition by the catalytic action of the enzyme. Quantification is achieved by measuring the time elapsed from addition of the substrate composition until a sudden color change discernible to the eye occurs. The measured time is then compared against a predetermined standard to determine the amount of antigen present in the sample.

8 Claims, 10 Drawing Sheets

Principle of an ELISA

Stage 1    Stage 2    Stage 3

Analyte

Antibody

E   Enzyme

Colour Reaction

Principle of a Chemical Clock

METHOD FOR QUANTITATIVE MEASUREMENT OF AN ENZYME LINKED IMMUNOSORBENT ASSAY

The present invention relates to a method of quantitative measurement of an enzyme linked immunosorbent assay.

The enzyme linked immunosorbent assay technique (ELISA) is an important analytical tool that is used in a wide variety of applications.

BRIEF DESCRIPTION OF THE DRAWINGS

FIG. 8 shows the effect of the level of potassium superoxide on the indicator tetrazolium.

FIG. 9 shows the effect of the level of xanthine oxidase on the time of color development.

Figure 1:
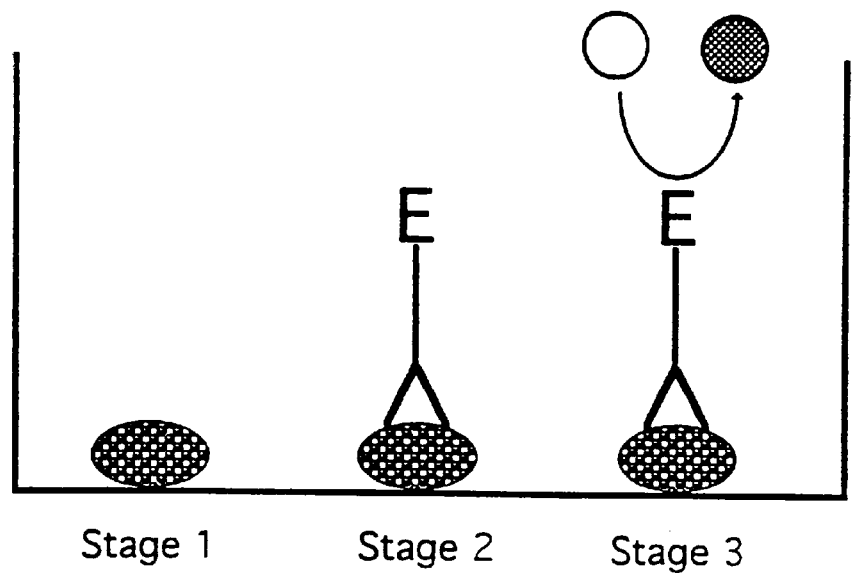
FIG. 1 is a pictorial representation of the basic principle of an ELISA.
Figure 1:
Figure 1:
Figure 1:
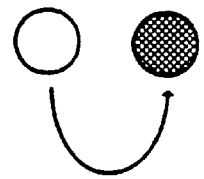

In one commonly used protocol the analyte or antigen to be quantified is attached to a solid support, for example in the well of a microtitre plate. The analyte may be immobilised by chemical reaction, by binding to an antibody (a so-called sandwich reaction) or by direct binding to the plastics surface by virtue of the innate "stickiness" of the analyte molecule.

Unoccupied binding sites on the surface are then blocked by flooding the plate with a non-specific protein. The analyte is then treated with an antibody that binds specifically avidly and tightly to the analyte. Any residual unbound antibody is washed off the plate. If no analyte was present to bind the antibody, all the antibody would be washed away. If a significant amount of analyte is present, a corresponding significant amount of antibody will bind to the plate. The quantity of antibody binding to the plate is determined by an enzymatic colour reaction.

In most cases and particularly with commercially available kits, the enzyme is chemically coupled to the antibody. A typical example would employ an antibody coupled to horse radish peroxidase. This enzyme oxidises a colorless substrate eg the dye ABTS to produce a coloured oxidation product. The colour forming reaction is permitted to proceed for some 30 minutes before being terminated by treatment with dilute acid. The quantity of color generated by the reaction may then be determined using a spectrophotometer. The amount of color generated corresponds directly to the amount of enzyme present and thus to the amount of bound antibody and to the amount of analyte of interest. This system allows quantitative analysis of an analyte of interest.

Use of the ELISA technique allows detection and quantification of a wide variety of molecular species and it is typically used to detect and quantify substances such as pesticides, mycotoxins, microbial cells or viruses. Because of the suitability of the ELISA technique for detecting analytes or antigens that would be difficult to assay by other methods dedicated ELISA systems are frequently sold as complete test kits and are often purchased on a "one-off" basis. However, all quantitative ELISA systems suffer from the same drawback that at the end of the analysis they require the use of spectrophotometric equipment for the final assessment and quantification step. Spectrophotometers are expensive pieces of equipment and may not always be available. This is especially likely given that the ELISA technique is particularly suited to one-off analysis. Moreover, in many cases the kits may be used to test for the particular analyte of interest in circumstances or at times when a spectrophotometer is unavailable, for example in field testing or in a manufacturing environment such as in a brewhouse.

It is an object of the present invention to provide a method of quantifying an enzyme linked immunosorbent assay that does not require spectrophotometric measurement.

According to the present invention there is provided a method of quantitative analysis of an immunoassay comprising the steps i) formation of antigen-antibody complex between antigen present in a sample and an enzyme labelled antibody;

ii) addition of substrate composition which can be converted into a differently coloured product composition by the catalytic action of the enzyme; characterised in that quantification is achieved by measuring the time elapsed from step (ii) until the color change occurs which color change being sudden and discernable by eye and then comparing the measured time against a predetermined reference standard to determine the amount of antigen present in the sample.

In some embodiments the step of forming the antigen antibody complex will comprise the following sub-steps:

a) coupling antibody to a solid support;

b) addition of sample to be quantified;

c) washing to remove unbound molecules;

d) addition of enzyme labelled second antibody; and e) washing to remove unbound enzyme labelled second antibody.

In alternative embodiments the step of forming the antigen-antibody complex will comprise the following sub-steps:

a) coupling the antigen present in the sample to a solid support;

b) washing to remove unbound molecules;

c) addition of enzyme-labelled antibody; and d) washing to remove unbound enzyme labelled antibody.

In further alternative embodiments the step of forming the antigen-antibody complex will comprise the following sub-steps:

a) coupling a known amount of antigen of interest to a solid support;

b) addition of enzyme labelled antibody pretreated with sample to be quantified; and c) washing to remove unbound enzyme labelled antibody.

According to the method of the present invention the time taken for the substrate composition to be converted to a differently coloured product composition must be proportional to the amount of antigen present in the sample. In the method of the present invention this is achieved by coupling the enzyme catalysed colour generating step to a chemical clock system.

Typically the ELISA system will be one of the aforementioned systems but it will be understood that other systems may be used provided they are capable of recognising an analyte by enzyme conjugated antibody.

Figure 2:
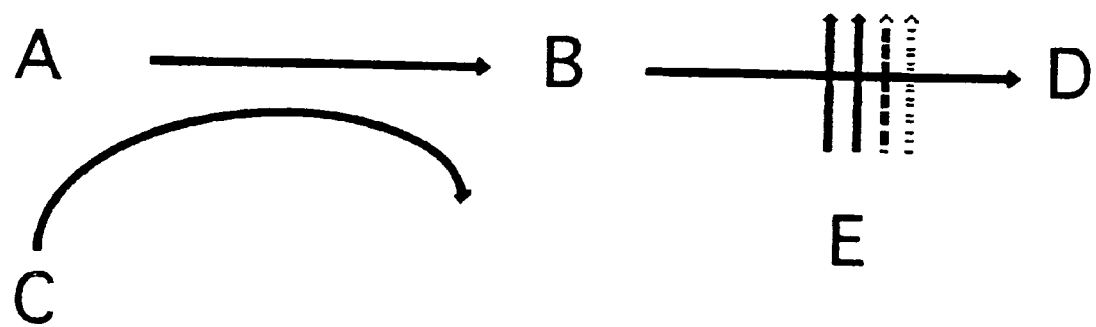
FIG. 2 is a pictorial illustration of the basic principle of a chemical clock.

The basic principle of a chemical clock is illustrated in FIG. 2.

Referring to FIG. 2, chemical A is converted to chemical B by reactant C. Reactant C may be for example a chemical, a reactive radical, or an enzyme. Chemical B is then able to react with chemical D to generate a color visible to the unaided eye. However it is temporarily prevented from reacting with D by the presence of chemical E. Chemical E may "mop up" chemical B by reacting directly with it, may convert chemical B to some other compound that cannot react with chemical D, or may return chemical B to chemical A.

Thus no color change will be observed whilst chemical E is present. However, as soon as chemical E is totally consumed, newly generated chemical B will react with chemical D, and a color change is observed. It is important that chemical E reacts avidly with chemical B whilst chemical B is present and it is also important that the quantity of chemical B required to effect a colour change is very small. Accordingly, chemical D should have the nature of an indicator reagent; able to show a small change in chemical B as a large change of color. In this way nothing appears to happen on initial mixing of the reagents but then the colour changes suddenly and intensely.

In these circumstances, it is possible to arrange reaction conditions so that the length of time required before a color change is observed depends upon the concentration of reactant C or on the concentration of chemical E. According to the method of the present invention the concentrations of either reactant C or chemical E can be modulated by an enzyme that is attached to an antibody. The enzyme may generate one of the rate limiting chemicals or it may remove one previously added. Examples of both of these mechanisms are given below.

In a first preferred embodiment of the invention the enzyme catalysed colour generating step is coupled to an iodine clock system.

With reference to the scheme shown in FIG. 2, the components of the iodine clock system are as follows:

Chemical A, Potassium Iodide, is converted to Chemical B, Iodine by Chemical C, Hydrogen Peroxide. Iodine is then able to react with Chemical D, Starch generating a blue color, however Chemical E, Sodium Thiosulphate, inhibits the colour generating reaction.

Only when all of the sodium thiosulphate is consumed by reaction with iodine does the excess iodine turn the starch blue. The amount of hydrogen peroxide present governs the speed at which this occurs since it converts potassium iodide to iodine. The amount of hydrogen peroxide present is governed by the presence of the enzyme catalase (an enzyme that degrades hydrogen peroxide to water) attached to an antibody.

Figure 3:
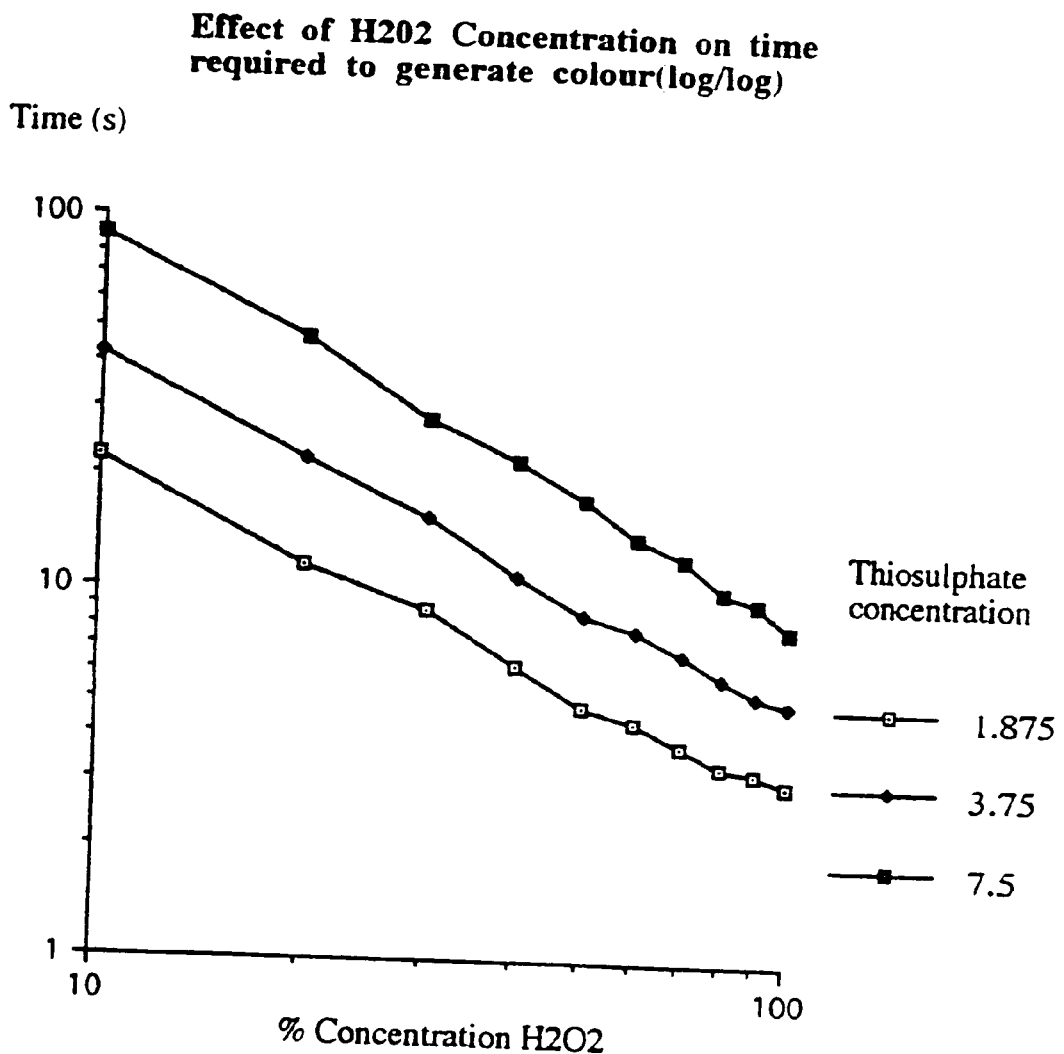
FIG. 3 is a graph showing the effect of hydrogen peroxide concentration in the reaction mixture on the time required for generation of color.

FIG. 3. shows the time required before color appears when different levels of hydrogen peroxide are present in the reaction mixture. The actual time that is required can be adjusted by varying the quantity of sodium thiosulphate (shown in the key).

Figure 3A:
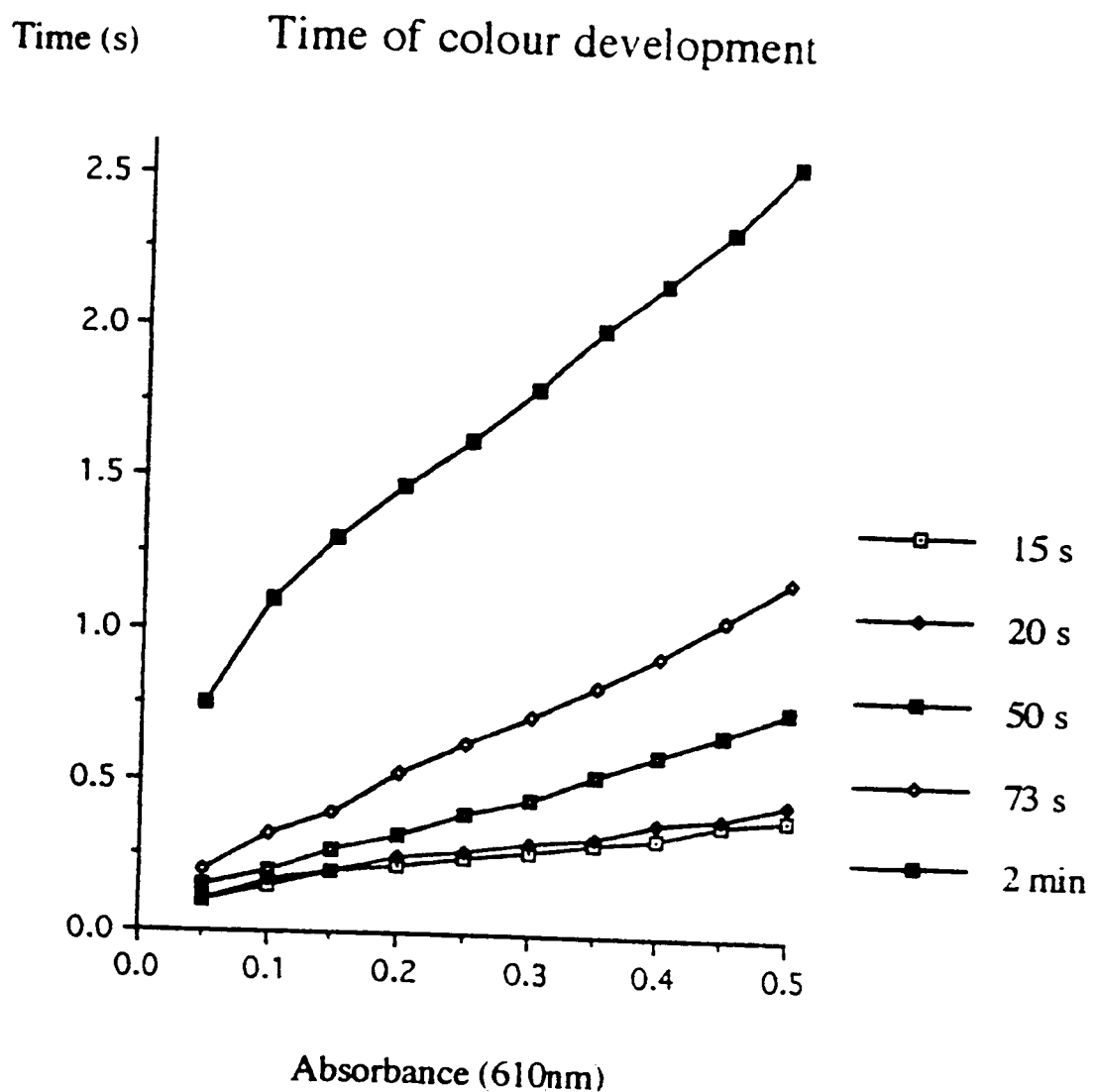
FIG. 3a is a graph showing the rate, expressed as the time of color development, at which 0.50 absorbance units at 610 nm were achieved after the addition of various amounts of hydrogen peroxide.

The time required before a color change occurred varied with the concentration of $H_2O_2$, as did the rate with which the color changed. To be of use the color change must be sufficiently rapid, even at low $H_2O_2$ concentrations, so that reliable timings can be made. Indecision as to whether a color change has or has not occurred must be avoided. FIG. 3a shows the rate at which 0.50 absorbance units at 610 nm were achieved after the addition of various amounts of $H_2O_2$. The different periods required before a colour change occurred has been omitted for reasons of clarity but is shown as a label on the graph. At high concentrations of $H_2O_2$ (ie at short reaction times) the rate of absorbance increase was extremely rapid. At 73.8 seconds, the longest time, the reaction developed 0.5 $A_{610}$ in 1.2 seconds. Even at a reaction time of two minutes, the time required to develop 0.5 $A_{610}$ was about 2.5 seconds, being only 2% of the total time required. In fact the unaided eye can detect absorbance changes that are much smaller than 0.5 $A_{610}$ and so the development time, even at the lower $H_2O_2$ concentrations encountered should not be a problem.

Figure 4:
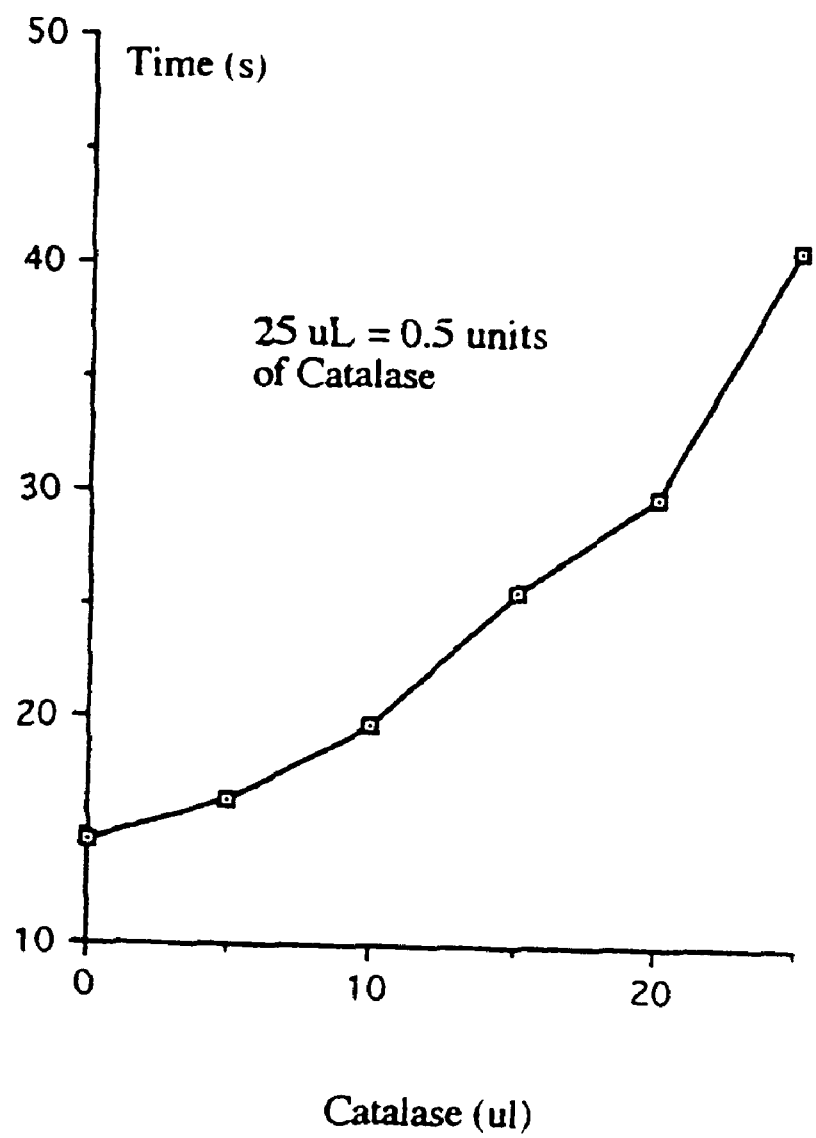
FIG. 4 is a graph showing the effect of various catalase levels on the reaction time required by the chemical clock to generate the blue color.

FIG. 4. shows that the reaction time can controlled by pre-incubation of the reaction mixture with catalase. The pre-incubation is terminated with dilute acid. The greater the quantity of catalase present, the longer the reaction time required by the chemical clock to generate the blue color. Excessively high levels of hydrogen peroxide may cause inactivation of the catalase. For this reason the level of peroxide and thiosulphate can be reduced. This has the advantage that lower levels of enzyme can be used but care has to be taken that, at longer reaction times, the development of color is sudden. The most suitable value was for 0.2 M $H_2O_2$ with 0.6 g/l (4.44 mM) Thiosulphate.

Figure 5:
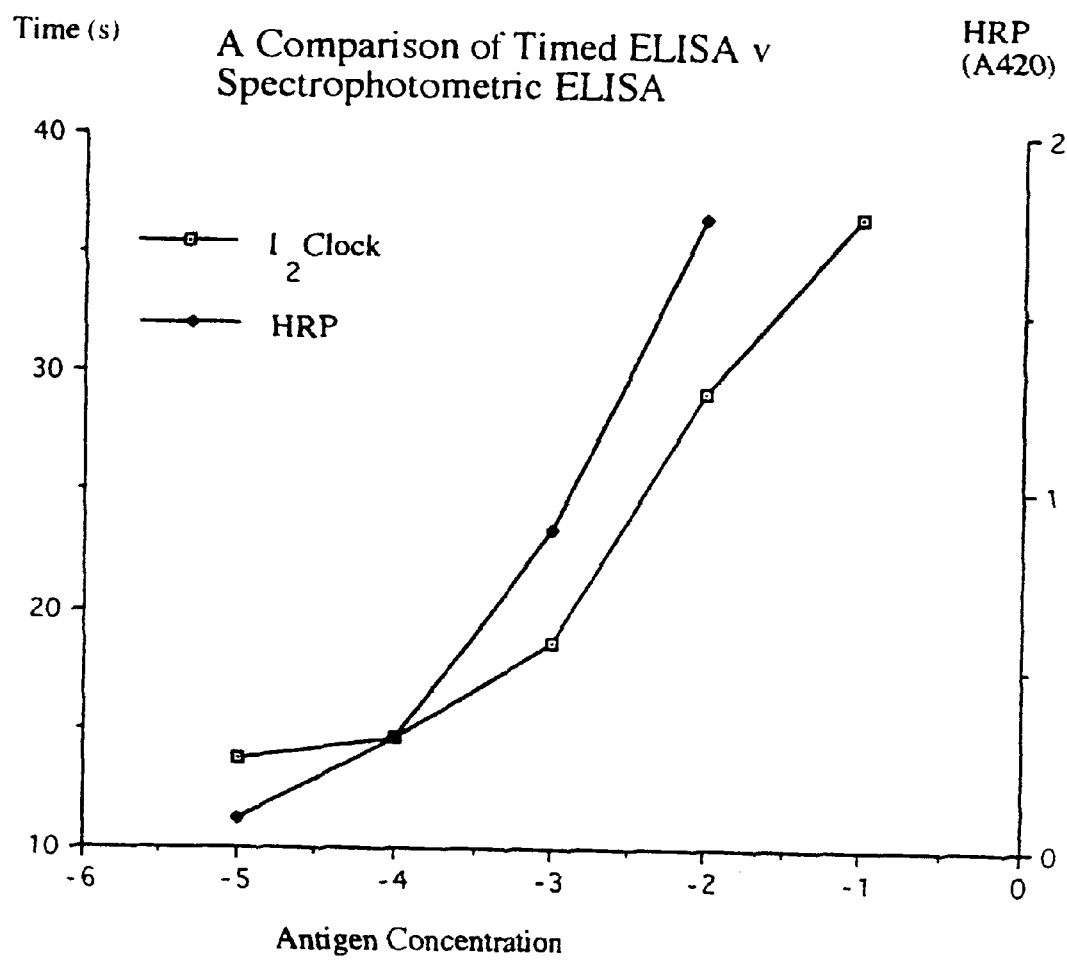
FIG. 5 is a graph showing a comparison of a titration of antigen based on the timed catalase/iodine clock system with a standard ELISA using a spectrophotmetric determination.

FIG. 5. shows a comparison of an example of a titration of antigen using the system of a preferred embodiment of the present invention based on the Catalase/Iodine clock system with a standard ELISA using spectrophotometric determination of Horse Radish Peroxidase conjugated antibody. The type of immunosorbent assay is shown in FIG. 1. The components were:

Analyte—Normal goat serum ($10^{-1}$ to $10^{-5}$ dilution).

Blocking agent—Milk Casein.

Antibody—Rabbit anti-goat IgG antibody.

Enzyme—Catalase.

Reaction—Hydrogen peroxide degraded to water followed by assessment using the Iodine clock.

All reactions were carried out in phosphate buffered saline (pH 6.8) (PBS).

The immunosorbent assay was conducted according to the following protocol:

A. All materials were supplied by the Sigma Chemical Company unless stated otherwise.

B. Conjugated Antibody.

Preparation of the catalase antibody was by a modification of the method of Avarameas S., Ternynck T. and Guesdon J. L. (Scandinavian Journal of Immunology Vol.8, Suppl.7, 7–23, 1978)

1. Antibody (Rabbit anti-goat IgG) was mixed with catalase in the ratio 1:2 by weight in 0.5 ml of phosphate buffered saline (PBS). This was dialysed overnight against 0.1 M PBS at 4° C.

2. A volume of 0.05 ml of a 1% v/v glutaraldehyde solution was added and the mixture stirred at room temperature for 3 hours.

3. A volume of 0.1 ml of a 1 M solution of lysine was added to the mixture which was stirred again at room temperature for another 2 hours.
4. The conjugate mixture was dialysed overnight against 0.1 M PBS at 4° C.
5. A sample of 0.2 ml of the conjugate mixture was applied to a Superose 6 size-exclusion chromatography column (Pharmacia, Uppsala, Sweden) to separate conjugate from unreacted antibody. Using PBS at a flow rate of 0.3 ml/minute, the protein peak corresponding to the largest molecular weight was collected and used for ELISA titrations. Attempts to use unseparated materials were unsuccessful.

C. Enzyme Linked Immunosorbent Assay Titrations

1. A serial dilution of normal goat serum in 0.1 ml of PBS was placed into the wells of a Microtitre ELISA plate and maintained at room temperature for 2 hours. The solutions were then shaken from the plate.
2. The wells were then blocked from further non-specific reaction with a solution of 0.1% w/v milk powder in PBS at room temperature for 1 hour. Again excess material was shaken from the plate.
3. The plate was washed 5 times with PBS containing 0.05% Tween 20.
4. A serial dilution of antibody enzyme conjugate in 0.1 ml of PBS was added to the wells to cross the dilutions of step 1. Again this was maintained at room temperature for 2 hours.
5. The plate was washed 5 times with PBS Tween and shaken dry.
6. A solution of 0.1 ml hydrogen peroxide (2% v/v) in 1/10 PBS Tween was added to each well and maintained at room temperature for i hour. Sodium perborate may be used instead of hydrogen peroxide. The reaction was terminated by the addition of 0.05 ml of 1 M sulphuric acid.
7. The remaining Peroxide was revealed by timing the iodine clock reaction ie the time elapsed from addition of the iodine clock components until the appearance of the blue color. The iodine clock compounds comprised 6% w/v potassium iodine, 0.6% w/v sodium thiosulphate and 0.04% w/v starch. Sodium carbonate may be included as a stabiliser.

The times shown in FIG. 5. are those in excess of the control reaction (no catalase) which required 13 seconds. The maximum level of goat antigen therefore gave a reaction time of 37 seconds (24 seconds longer than the control) with 1/10 dilution of the conjugate. Undiluted conjugate gave considerably longer times. It may be noticed that the results of FIG. 5. (antibody bound catalase) resembles very closely the results of FIG. 4. (pre-incubation with free catalase) indicating the similarity of reaction. Also shown on this graph is the same reaction visualised by the spectrophotometric technique using Horse Radish Peroxidase conjugated antibody (from a commercial source). At dilutions of 1/10 conjugate the two systems compared well. Both were able to detect normal goat serum at $10^{-3}$ dilution. By using the conjugate undiluted the timed ELISA system was able to detect normal goat serum at $10^{-4}$ dilution (17 seconds), a performance equal to that of the horse radish peroxidase system. In order to ensure that typical antigen levels encountered give results in a useful timescale, careful adjustment of the timed ELISA reagent concentrations is required.

The variability of the timed ELISA system was monitored at seconds (zero control) and at 60 seconds (typical of a low positive value). The zero control gave a relative standard deviation of 11.4% (n=10, x=13.9 s, s.d.=0.15 s) across a row of a microtitre plate and 15.8% (n=8, x=14.1 s, s.d.=0.22 s) down a column. The positive value had a relative standard deviation across a row of 9.5% (n=9, x=57.0 s, s.d.=5.4 s) and 4.7% down a column (n=8, x=55.4 s, s.d.=2.6 s).

From the results obtained it seems that the standard ELISA is slightly more sensitive than the timed ELISA but the difference is small. The maximum sensitivity that can be achieved with the timed ELISA method of the present invention depends on the efficiency of the enzyme antibody conjugation, a procedure that has not yet been optimised for catalase.

In a second preferred embodiment of the invention the enzyme catalysed color generating step is coupled to a pH clock system.

With reference to the scheme shown in FIG. 2 the components of the pH clock system are as follows:

Chemical A, alcohol, is converted to acetaldehyde with production of Chemical B, Hydrogen ions, by the influence of Reagent C, Alcohol dehydrogenase. The hydrogen ions react with Chemical D, a pH indicator, generating a change in color. However Chemical E, a pH buffer prevents this reaction.

In this case it is the alcohol dehydrogenase that is coupled to the antibody.

The specific nature of chemicals D and E depends on the pH performance of the alcohol dehydrogenase. Alcohol dehydrogenase from yeast has a maximum activity at pH 8.8 thus a buffer of glycine—NaOH will bracket this pH. (Glycine has two pka values at 2.35 or 9.78 with a pH buffering action at either ⁻2.2–3.6 or ⁻8.6–10.6). Neutral red would be a useful indicator.

In this embodiment of the enzyme linked immunosorbent assay of the invention alcohol dehydrogenase, which is bound to the analyte or antigen by the antibody, catalyses the production of hydrogen ions promoting a drop in pH. However the buffer will tend to prevent the pH drop (for a short time) while the system is near the pka of the glycine. As the system moves away from the pka, the pH changes rapidly towards the lower pka causing the indicator (Neutral red) to change color.

Figure 6:
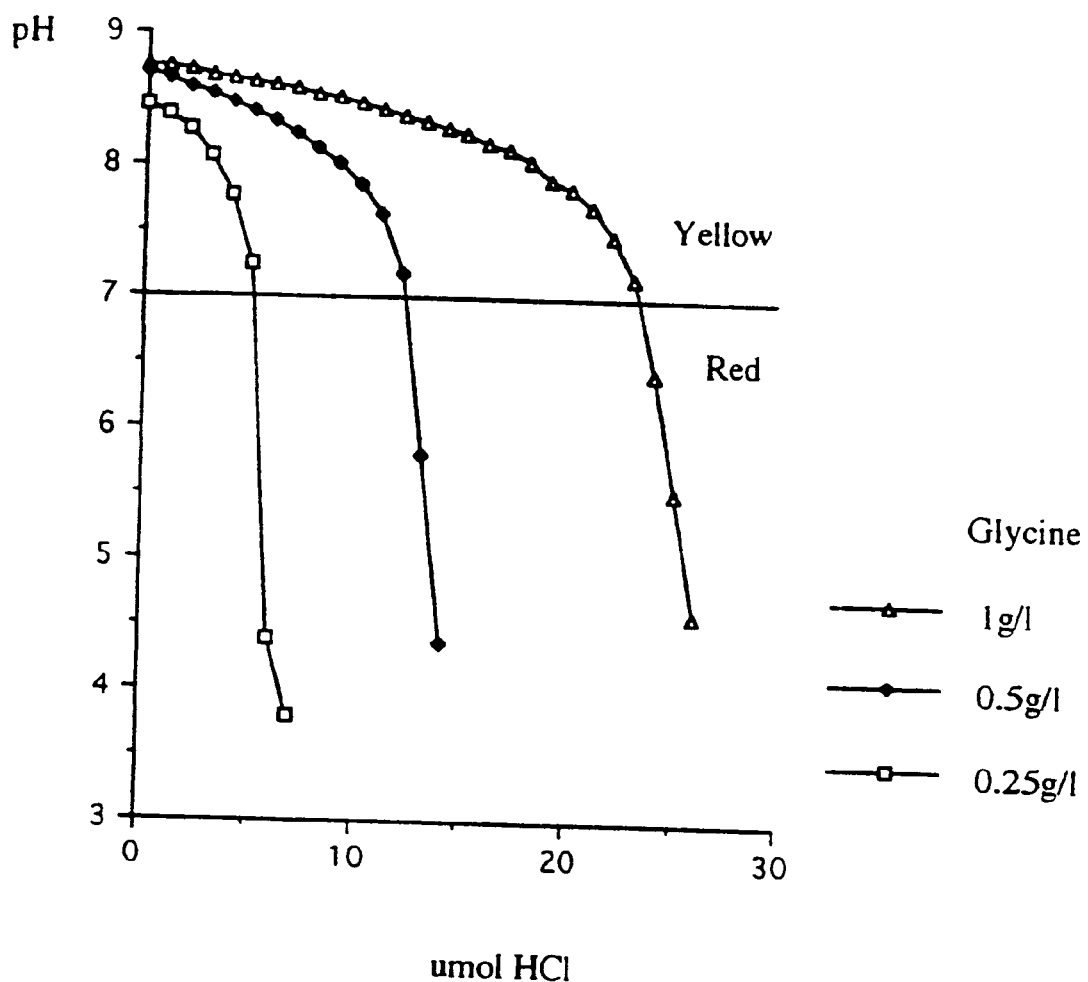
FIG. 6 is a graph showing the effect of the addition of hydrochloric acid to a glycine buffer containing Neutral red indicator.

FIG. 6. shows the effect of adding hydrogen ions (as hydrochloric acid) to a glycine buffer containing Neutral red indicator. The pH remains steady for a period and then drops rapidly. (This Figure is the equivalent of FIG. 3).

Figure 7:
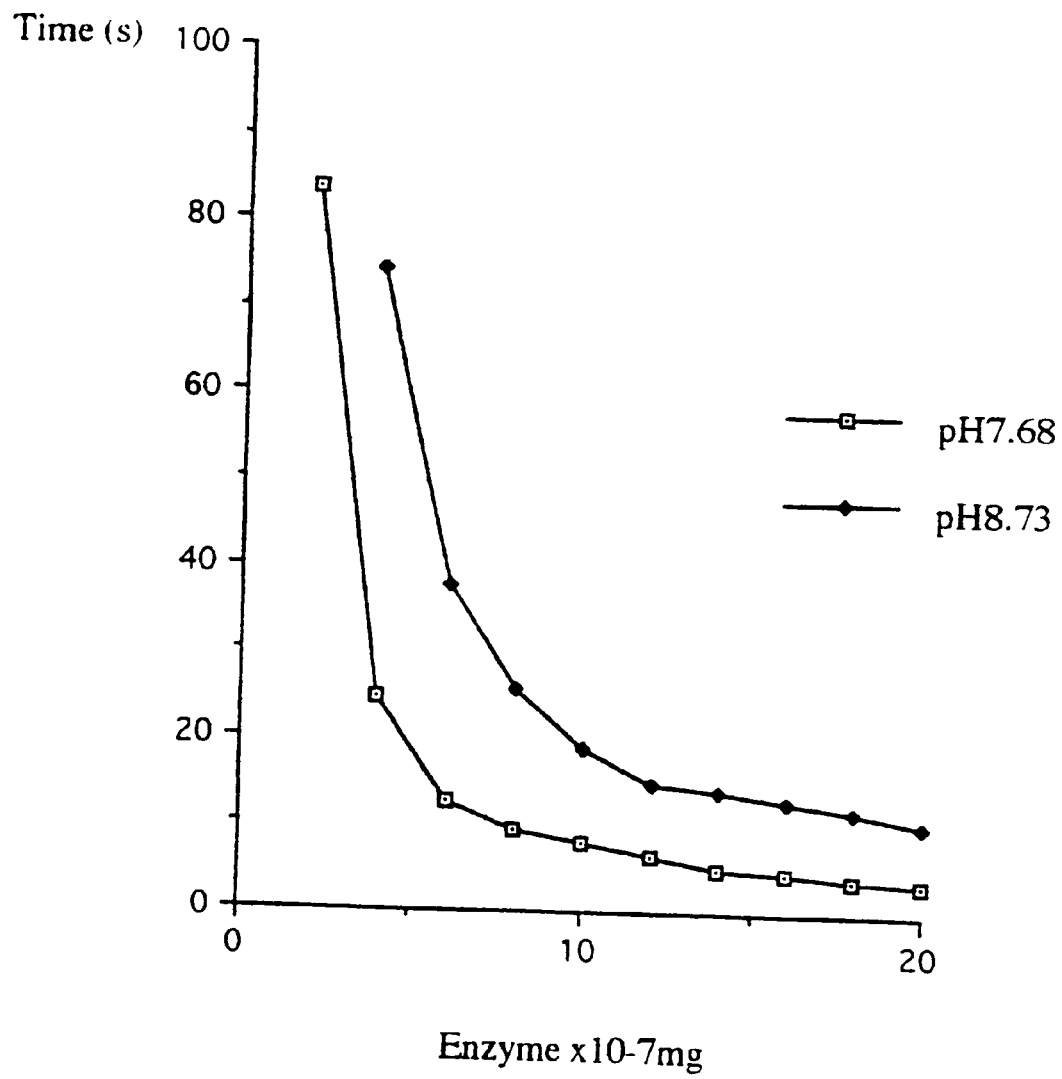
FIG. 7 is a graph showing the effect of alcohol dehydrogenase on the pH clock at a pH of 7.68 and 8.73.

FIG. 7. shows that the pH change, and hence the color of the indicator can be manipulated by the addition of alcohol dehydrogenase with ethanol and NAD. The graph shows the length of time required before the pH indicator changed from yellow to red when increasing amounts of enzyme were added to the system and is the equivalent of FIG. 4.

The same reaction can be achieved when the alcohol dehydrogenase is bound directly to the solid support for example a microtitre plate.

In a further preferred embodiment of the invention the enzyme catalysed colour generating step is coupled to a redox clock system.

With reference to the scheme shown in FIG. 2 the components of the redox clock system are as follows:

Chemical A, Xanthine, is reduced yielding Chemical B, the superoxide radical, by the influence of Reagent C, Hypoxanthine oxidase. The superoxide radicals react with Tetrazolium salt (2,3,5 Triphenyl tetrazolium chloride) to generate a color change. However Chemical E, Tiron, (4,5 Dihydroxy-1,3-benzene disulphonic acid) prevents this reaction.

In this case it is the enzyme Hypoxanthine oxidase that is coupled to the antibody.

Typically the chemical clock systems will be the three aforementioned systems but it will be understood that other systems may be used provided they are capable of being coupled to an enzyme catalysed colour generating step.

Figure 8:
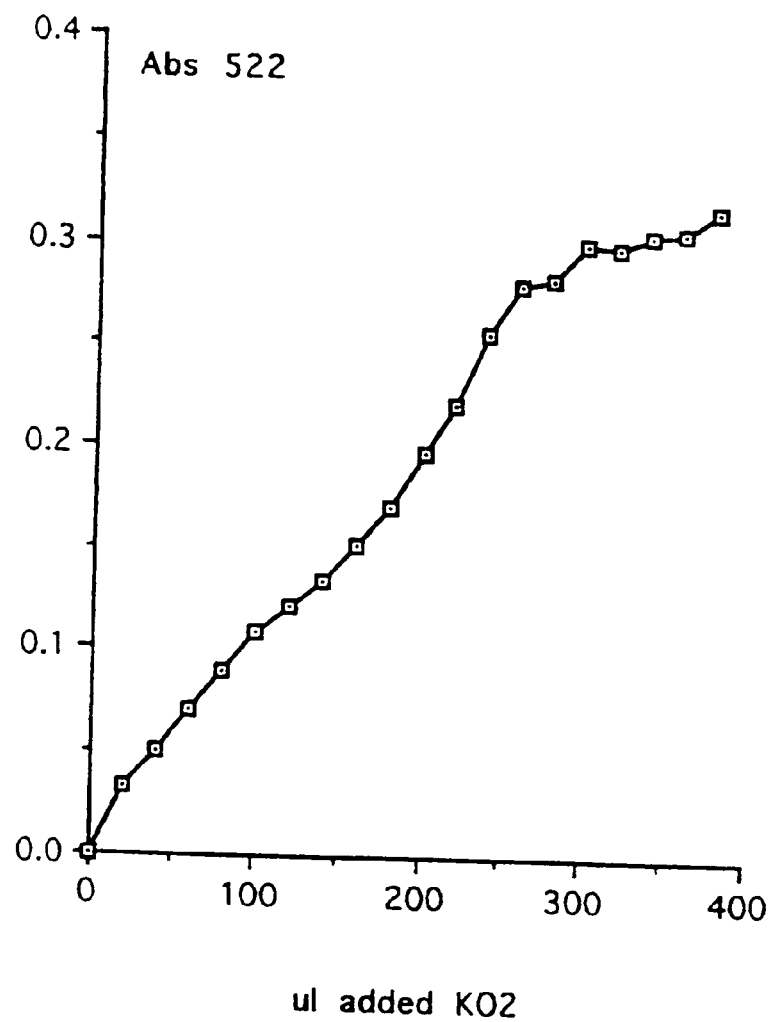
FIG. 8 is a graph which is equivalent to FIG. 3.

FIG. 8 shows the effect of adding increasing levels of potassium superoxide on the indicator tetrazolium. (This figure is equivalent to FIG. 3).

Figure 9:
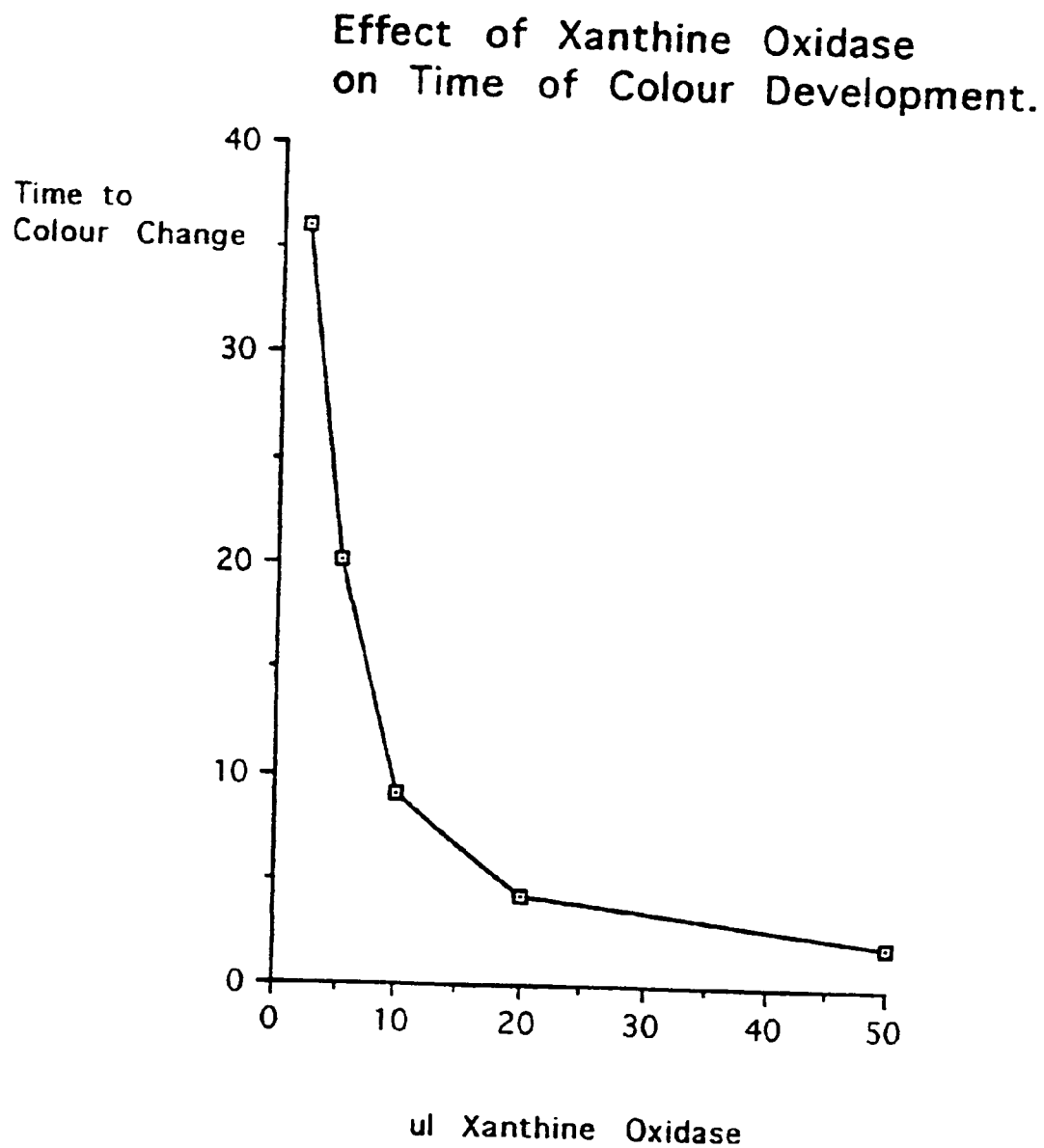
FIG. 9 is a graph which is equivalent to FIG. 4.

FIG. 9 shows the effect of adding increasing levels of xanthine oxidase on the time lag before a color change was observed. (This Figure is equivalent to FIG. 4).

I claim:

1. A method for the quantitative analysis of an immunoassay comprising the steps of:
   i) forming an antigen-antibody complex between an antigen present in a sample and an enzyme labelled antibody;
   ii) adding a substrate composition which can be converted into a differently colored product by the catalytic action of the enzyme, said substrate composition being coupled to a chemical clock system having a period capable of being modified by the enzyme, said chemical clock system comprising a chemical which is capable of being consumed and which prevents conversion of the substrate composition into said differently colored product until such time that the chemical is consumed, wherein the quantitative analysis is achieved by measuring the time elapsed from the addition of the substrate composition until a color change occurs which is associated with the appearance of said differently colored product and which is sudden and discernible by eye, and thereafter comparing said time against a reference standard to determine the amount of antigen present in the sample.

2. The method of claim 1 wherein the step of forming the antigen-antibody complex comprises the following steps:
   a) coupling an antibody to a solid support;
   b) adding the sample;
   c) washing to remove any unbound molecules;
   d) adding an enzyme labelled second antibody; and
   e) washing to remove any unbound enzyme labelled second antibody.

3. The method of claim 1 wherein the step of forming the antigen-antibody complex comprises the following steps:
   a) coupling the antigen present in the sample to a solid support;
   b) washing to remove any unbound molecules;
   c) adding the enzyme labelled antibody; and
   d) washing to remove any unbound enzyme labelled antibody.

4. The method of claim 1 wherein the step of forming the antigen-antibody complex comprises the following steps:
   a) coupling a known amount of an antigen to a solid support;
   b) adding an enzyme labelled antibody which has been pretreated with the sample; and
   c) washing to remove any unbound enzyme labelled antibody.

5. The method of claim 1 wherein the antibody is labelled with catalase and the substrate composition comprises potassium iodide, hydrogen peroxide and sodium thiosulphate.

6. The method of claim 1 wherein the antibody is labelled with alcohol dehydrogenase and the substrate composition comprises an alcohol, a pH indicator and a pH buffer.

7. The method of claim 6 wherein the pH indicator is neutral red and the pH buffer is glycine-sodium hydroxide.

8. The method of claim 1 wherein the antibody is labelled with hypoxanthine oxidase and the substrate composition comprises xanthine, a tetrazolium salt and 4,5-dihydroxy-1,3-benzene disulphonic acid.

* * * * *